US012312422B2

(12) United States Patent
Sanchez et al.

(10) Patent No.: US 12,312,422 B2
(45) Date of Patent: May 27, 2025

(54) CHITIN AND PROCESS FOR PRODUCING CHITIN AND/OR CHITOSAN BY THE ENZYMATIC AND CHEMICAL PATHWAY

(71) Applicant: Ynsect, Évry-Courcouronnes (FR)

(72) Inventors: Lorena Sanchez, Juvisy-sur-Orge (FR); Cecilia Socolsky, Lille (FR); Valérie Alezra, Paris (FR); Corentin Le Berre, Juvisy-sur-Orge (FR); Bénédicte Lorette, Montlhery (FR); Sophie Laurent, Nantes (FR); Nathalie Berezina, Paris (FR)

(73) Assignee: Ynsect, Évry-Courcouronnes (FR)

( * ) Notice: Subject to any disclaimer, the term of this patent is extended or adjusted under 35 U.S.C. 154(b) by 0 days.

(21) Appl. No.: 18/404,047

(22) Filed: Jan. 4, 2024

(65) Prior Publication Data

US 2024/0150498 A1 May 9, 2024

Related U.S. Application Data

(62) Division of application No. 16/772,423, filed as application No. PCT/FR2018/053285 on Dec. 31, 2018, now Pat. No. 11,958,918.

(30) Foreign Application Priority Data

Dec. 15, 2017 (FR) ...................................... 1762307

(51) Int. Cl.
  C08B 37/08 (2006.01)
  C08B 37/00 (2006.01)
  C08L 5/08 (2006.01)

(52) U.S. Cl.
  CPC ........ C08B 37/003 (2013.01); C08B 37/0003 (2013.01); C08L 5/08 (2013.01); C12Y 304/00 (2013.01)

(58) Field of Classification Search
  None
  See application file for complete search history.

(56) References Cited

U.S. PATENT DOCUMENTS

| 9,433,698 B2 * | 9/2016 | Ingber ........................ A61P 1/02 |
| 11,229,724 B2 * | 1/2022 | McGrath ............... C08B 37/003 |
| 11,667,927 B2 * | 6/2023 | Cordova-Kreylos ........................ C12Y 302/01014 800/279 |
| 11,958,918 B2 * | 4/2024 | Sanchez ................ C08B 37/003 |

FOREIGN PATENT DOCUMENTS

| CN | 1594368 A | 3/2005 |
| CN | 101045739 A | 10/2007 |
| CN | 101144097 | 3/2008 |
| CN | 10405739 | 9/2014 |
| CN | 106749761 A | 5/2017 |
| FR | 3031114 A1 | 7/2016 |
| FR | 3031115 A1 | 7/2016 |
| RU | 2067588 C1 | 10/1996 |

OTHER PUBLICATIONS

Abidin et al., *The Potential of Insects as Alternative Sources of Chitin: An Overview on the Chemical Method of Extraction from Various Sources*, 21, 4978 International Journal of Molecular Sciences 1-25 (2020).

Mohan et al., *Recent insights into the extraction, characterization, and bioactivities of chitin and chitosan from insects*, 105 Trends in Food Science & Technology 17-42 (2020).

Nahar et al., *The extracellular constitutive production of chitin deacetylase in Metarhizium anisopliae: possible edge to entomopathogenic fungi in the biological control of insect pests*, 85 Journal of Invertebrate Pathology 80-88 (2004).

Nwe et al., *Chitin and Chitosan from Terrestrial Organisms*, Chitin, 1.2.2 Chitosan, Oligosaccharides and Their Derivatives, 3-10 (Oct. 2010).

*Preparing chitin, chitosan and its oligosaccharide, involves performing micronization for materials, grinding granules into superfine powder, de-calcifying superfine powder, zymohydrolysis and removing protein to obtain chitin*, Thompson Scientific, London, GB, Database WPI XP002783789 (2009).

Quan et al., *Characterization of a spruce budworm chitin deacetylase gene: Stage- and tissue-specific expression, and inhibition using RNA interference*, 43 Insect Biochemistry and Molecular Biology 683-693 (2013).

\* cited by examiner

*Primary Examiner* — Hope A Robinson
(74) *Attorney, Agent, or Firm* — Panitch Schwarze Belisario & Nadel LLP; Erin M. Dunston

(57) ABSTRACT

The present invention relates to chitin with a differential purity of more than 97.75% and to a process for producing chitin and/or chitosan by the enzymatic and chemical pathway.

7 Claims, No Drawings

CHITIN AND PROCESS FOR PRODUCING CHITIN AND/OR CHITOSAN BY THE ENZYMATIC AND CHEMICAL PATHWAY

CROSS-REFERENCE TO RELATED APPLICATIONS

This application is a Divisional Application based on U.S. patent application Ser. No. 16/772,423, filed on Jun. 12, 2020, now U.S. Pat. No. 11,958,918, which is a U.S. National Stage Application pursuant to 35 U.S.C. § 371 of International Patent Application PCT/FR2018/053285, filed on Dec. 13, 2018, and published as WO 2019/115970 on Jun. 20, 2019, which claims priority to French Patent Application 1762307, filed on Dec. 15, 2017, all of which are incorporated herein by reference in their entireties for all purposes.

The present invention relates to a chitin, a chitosan and a method for preparing chitin and/or chitosan from insects.

According to the invention, by "chitin" is meant a polymer predominantly composed of glucosamine and N-acetyl glucosamine units, wherein said units can optionally be substituted by amino acids and/or peptides.

By "predominantly composed" is meant that said polymer contains between 55% and 98% by weight, preferably between 75 and 90% by weight, glucosamine and N-acetyl glucosamine units.

Chitin is said to be the second most synthesized polymer in the living world, after cellulose. In fact, chitin is synthesized by a number of species in the living world: it constitutes part of the exoskeleton of crustaceans and insects and the side wall that surrounds and protects fungi. More particularly, in insects, chitin thus constitutes 3 to 60% of their exoskeleton.

By "chitosan" is meant, according to the present invention, the products of deacetylation of chitin. The usual limit between chitosan and chitin is determined by the degree of acetylation: a compound having a degree of acetylation lower than 50% is called chitosan, beyond that a compound having a degree of acetylation higher than 50% is called chitin.

The applications of chitin and/or chitosan are numerous: cosmetic (cosmetic composition), medical and pharmaceutical (pharmaceutical composition, treatment for burns, biomaterials, corneal dressings, surgical threads), dietary and food (human foodstuffs in particular in œnology and animal nutrition, more specifically in aquaculture and aviculture), technical (filtering, texturing, flocculating or adsorbing agent in particular for water filtration and water pollution control), etc. In fact, chitin and/or chitosan are biocompatible, biodegradable and non-toxic materials.

Usually, chitin and chitosan are obtained from different species that synthesize chitin, such as those mentioned above, and in particular from crustaceans or insects.

It is particularly advantageous to obtain chitin and chitosan from insects, as the latter represent an abundant and renewable raw material.

In a number of applications, such as for example cosmetics and pharmacy, it is desired to obtain a chitin and/or a chitosan with a high purity. A high purity limits in particular the risks of allergies, and of local or generalized fever, associated with the application of cosmetic or pharmaceutical products containing chitin and/or chitosan. Such reactions can in fact be triggered by impurities such as residual amino acids, ash or lipids.

The invention therefore relates to a chitin, the purity by difference of which is greater than 97.75%.

Within the framework of the present application, in order to measure the purity, the known impurity contents, namely amino acids, lipids and ash are subtracted from the absolute purity value (100%) in order to obtain the value of the estimated purity by difference. Thus, for example, a sample which contains 30% amino acids, 10% lipids and 1% ash is consequently attributed a purity by difference of 100−30−10−1=59%.

The chitin according to the invention, which has a high purity by difference, thus has low amino acid, lipid and ash contents.

The chitin according to the invention advantageously has a purity by difference greater than or equal to 98%, preferably greater than or equal to 98.1%.

The amino acid content of the chitin according to the invention is preferably determined according to the method NF EN ISO 13904 for tryptophan and NF EN ISO 13903 for the other amino acids.

The relative abundance, expressed in percent, can be calculated by relating each amino acid content to the total amino acid content.

Throughout the application, where no date has been specified for a regulation, a standard or a directive, the regulation, standard or directive in force at the filing date is meant.

The methods for determining the fat (lipid) content are well known to a person skilled in the art. By way of example and preferably, the determination of this content will be carried out by adapting the method from EC 152/2009 regulation.

The method for determining the ash content is well known to a person skilled in the art. Preferably, this content is determined according to the NF V18-101 standard.

Advantageously, the chitin according to the invention contains less than 1.2% by weight amino acids relative to the total dry weight of chitin.

Preferably, the chitin according to the invention contains less than 1% by weight, more preferentially less than 0.9% by weight, still more preferentially less than 0.8% by weight, and still more preferentially less than 0.75% by weight, amino acids relative to the total dry weight of chitin.

Advantageously, the residual amino acids present in the chitin according to the invention are: threonine, serine, glycine, glutamic acid, alanine, cysteine, valine, isoleucine, aspartic acid, leucine, tyrosine, phenylalanine, histidine, lysine, tryptophan or a combination of two or more thereof. Preferably, the residual amino acids present in the chitin according to the invention consist of: cysteine, valine, histidine, lysine, tryptophan or a combination of two or more thereof, preferentially of a combination of all of these amino acids.

Advantageously, the chitin according to the invention contains less than 2% by weight ash relative to the total dry weight of chitin.

The chitin according to the invention preferably contains less than 1.6% by weight, more preferentially less than 1.4% by weight, still more preferentially less than 1.2% by weight, ash relative to the total dry weight of chitin.

Advantageously, the chitin according to the invention contains less than 1% by weight, preferably less than 0.5% by weight, more preferentially less than 0.2% by weight, lipids relative to the total dry weight of chitin.

Still more preferentially, the chitin according to the invention does not contain any lipids.

Advantageously, the chitin according to the invention has a molecular mass greater than or equal to 450 kg·mol$^{-1}$, preferably greater than or equal to 500 kg·mol$^{-1}$, more preferentially greater than or equal to 600 kg·mol$^{-1}$, still more preferentially greater than or equal to 650 kg·mol$^{-1}$.

The molecular mass is determined using the falling ball viscosity measurement.

Preferably, the molecular mass is determined according to a falling ball viscosity measurement method based on the one described in the following publication: "Pacheco et al.; *Structural characterization of chitin and chitosan obtained by biological and chemical methods; Biomacromolecules;* 12, 3285-3290, 2011".

In particular, this method is used in Example 1.

Preferably, the chitin according to the invention is an isolated chitin.

By "isolated" chitin is meant a chitin which has been isolated or extracted from its natural environment.

More particularly, within the framework of the present application, the chitin is isolated or extracted from insects, more specifically from insect cuticles.

According to a preferred embodiment, the chitin has a purity by difference greater than or equal to 98.0% and advantageously a molar mass greater than or equal to 800 kg·mol$^{-1}$, a purity by difference greater than or equal to 98.5% and advantageously a molar mass greater than or equal to 850 kg·mol$^{-1}$.

According to this preferred embodiment, the chitin advantageously contains less than 0.35% by weight amino acids relative to the total dry weight of chitin, and/or less than 0.9% by weight ash relative to the total dry weight of chitin, and/or less than 0.3% by weight lipids relative to the total dry weight of chitin.

The invention also relates to a chitosan, the purity by difference of which is greater than 97.75%.

Preferably, the purity by difference of the chitosan according to the invention is greater than or equal to 98%, more preferentially greater than or equal to 98.1%.

The purity by difference, the amino acid content, the ash content, and the lipid content of the chitosan according to the invention are measured in the same manner as indicated above for the chitin.

Advantageously, the chitosan according to the invention contains less than 0.8% by weight amino acids relative to the total dry weight of chitosan.

Preferably, the chitosan according to the invention contains less than 0.6% by weight, and more preferentially less than 0.4% by weight, amino acids relative to the total dry weight of chitosan.

Advantageously, the residual amino acids present in the chitosan according to the invention are: threonine, tyrosine, lysine and/or tryptophan.

Advantageously, the chitosan according to the invention contains less than 2% by weight ash relative to the total dry weight of chitosan.

The chitosan according to the invention preferably contains less than 1.8% by weight, more preferentially less than 1.5% by weight, still more preferentially less than 1.0% by weight, ash relative to the total dry weight of chitosan.

Advantageously, the chitosan according to the invention contains less than 1% by weight, preferably less than 0.7% by weight, more preferentially less than 0.5% by weight, lipids relative to the total dry weight of chitosan.

Advantageously, the chitosan according to the invention has a molecular mass greater than or equal to 250 kg·mol$^{-1}$, preferably greater than or equal to 300 kg·mol$^{-1}$, more preferentially greater than or equal to 350 kg·mol$^{-1}$, still more preferentially greater than or equal to 400 kg·mol$^{-1}$.

Preferably, the chitosan according to the invention is an isolated chitosan.

By "isolated" chitosan is meant a chitosan which has been obtained from a chitin isolated or extracted from its natural environment.

More particularly, within the framework of the present application, the chitosan is obtained from a chitin isolated or extracted from insects, more specifically from insect cuticles.

According to a preferred embodiment, the chitosan has a purity by difference greater than or equal to 97.9% and a molar mass greater than or equal to 480 kg·mol$^{-1}$, more particularly a purity by difference greater than or equal to 98.8% and a molar mass greater than or equal to 540 kg·mol$^{-1}$.

According to this preferred embodiment, the chitosan advantageously contains less than 0.4% by weight amino acids relative to the total dry weight of chitosan, and/or less than 0.6% by weight ash relative to the total dry weight of chitosan, and/or less than 0.2% by weight lipids relative to the total dry weight of chitosan.

The invention also relates to a method for obtaining chitin and/or chitosan, from insects, comprising the following steps:
- separation of the cuticles from the soft part of the insects,
- enzymatic hydrolysis of the cuticles by a protease, in order to obtain a solid residue, and
- basic treatment of the solid residue.

The method for obtaining chitin and/or chitosan according to the invention makes it possible to obtain a chitin and/or a chitosan with a high purity.

Moreover, the method according to the invention, and more particularly the enzymatic hydrolysis step, makes it possible to reduce certain drawbacks inherent in the subsequent step of basic treatment, such as for example to reduce the quantity of base used during this step. This step also makes it possible to recover a hydrolysate.

Advantageously, the method according to the invention does not comprise an oxidation step, such as for example a treatment with hydrogen peroxide.

By "insects" is meant insects at any stage of development, such as an adult stage, a larval stage or a nymph stage (intermediate stage). Advantageously, the insects used in the method according to the invention are at a larval stage if the insects are holometabolous, at a nymph stage (intermediate stage) if the insects are heterometabolous, or at an adult stage where appropriate.

The insects used in the method according to the invention can be edible.

Advantageously, the insects preferred for use in the method according to the invention are for example coleopterans (beetle), dipterans, lepidopterans (such as for example *Galleria mellonella*), isopterans, orthopterans, hymenopterans, blattopterans, hemipterans, heteropterans, ephemeropterans and mecopterans, preferably coleopterans, dipterans, orthopterans, lepidopterans or mixtures thereof, still more preferentially coleopterans.

The coleopterans preferentially used in the method according to the invention belong to the families Tenebrionidae, Melolonthidae, Dermestidae, Coccinellidae, Cerambycidae, Carabidae, Buprestidae, Cetoniidae, Dryophthoridae, or mixtures thereof.

More preferentially, they are the following coleopterans: *Tenebrio molitor, Alphitobius diaperinus, Zophobas morio, Tenebrio obscurus, Tribolium castaneum, Pachnoda marginata* and *Rhynchophorus ferrugineus*, or mixtures thereof. Still more preferentially, they are *Tenebrio molitor*.

The method for obtaining chitin and/or chitosan according to the invention comprises a step of separating the cuticles from the soft part of the insects.

The cuticle is the external layer (or exoskeleton) secreted by the epidermis of insects. In general it is formed of three layers: the epicuticle, the exocuticle and the endocuticle.

By "soft part" is meant the flesh (comprising in particular the muscles and the viscera) and the juice (comprising in particular body fluids, water and haemolymph) of insects. In particular, the soft part does not consist of the juice of the insects.

The separation of the cuticles from the soft part of the insects can be performed using any suitable type of separator.

According to a first embodiment, the separation of the cuticles from the soft part is carried out using a belt separator.

According to a second embodiment, the separation of the cuticles from the soft part is carried out using a filter press.

This step of separating the cuticles from the soft part of the insects is described more fully in step 2 of the detailed method for obtaining chitin and/or chitosan according to the invention hereafter.

This separation of the cuticles from the soft part of the insect makes it possible in particular to separate the chitin from the soft part. In fact, the cuticles obtained at the end of this separation step have a high chitin content of the order of 10 to 30% by weight relative to the total weight of cuticles, as indicated hereafter.

In particular, the step of separating the cuticles from the soft part is performed without any prior step of grinding the insects, in particular in the form of particles, having been performed.

The method for obtaining chitin and/or chitosan according to the invention advantageously comprises a killing step prior to the step of separating the cuticles from the soft part.

This killing step is described more fully in step 1 of the detailed method for obtaining chitin and/or chitosan according to the invention hereafter.

Advantageously, following killing step 1, the insects are directly used to carry out step 2 of separating the cuticles from the soft part of the insects, i.e. the insects are not subjected to any treatment, such as grinding, freezing or dehydration, between step 1 and step 2.

The method for obtaining chitin and/or chitosan according to the invention comprises a step of enzymatic hydrolysis of the cuticles by a protease, in order to obtain a solid residue, following the step of separating the cuticles from the soft part of the insects.

Advantageously, the enzymatic hydrolysis is performed for a duration comprised between 3 and 10 hours, preferentially comprised between 4 and 8 hours, such as for example of the order of 6 hours.

It will be noted that, within the framework of the present application, and unless stipulated otherwise, the ranges of values indicated are understood to be inclusive.

Preferably, the enzymatic hydrolysis is carried out at a temperature comprised between 4° and 80° C., preferentially comprised between 5° and 70° C., such as for example approximately 60° C.

Advantageously, the enzymatic hydrolysis is carried out at a pH comprised between 6 and 8, preferentially between 6.5 and 7.5.

The enzymatic hydrolysis can be carried out with a single protease or alternatively with a mixture of enzymes containing at least one protease, more preferentially a mixture of enzymes containing several proteases, such as a mixture containing an endoprotease and an exoprotease, or a protease and a polysaccharase.

The enzyme or the mixture of enzymes is introduced in a quantity ranging from 0.2 to 10% by weight, preferentially from 1 to 8% by weight, more preferentially from 3 to 7% by weight, relative to the weight of (wet) cuticles subjected to the enzymatic hydrolysis.

In terms of enzymatic activity, the quantity of enzyme or mixture of enzymes introduced is equivalent to an activity comprised between 2000 and 5000 SAPU ("Spectrophotometric Acid Protease Unit"), preferably comprised between 3000 and 4000 SAPU, per 100 g by wet weight, with a moisture content of from 30 to 70%, of substrate to be converted, i.e. of insect cuticles.

This step of enzymatic hydrolysis of the cuticles is described more fully in step 3 of the detailed method for obtaining chitin and/or chitosan according to the invention hereafter.

The method for obtaining chitin and/or chitosan according to the invention comprises a step of basic treatment of the solid residue, following the step of enzymatic hydrolysis of the cuticles.

Advantageously, the basic treatment is carried out using a strong base.

Advantageously, the strong base is chosen from sodium hydroxide or caustic soda, potassium hydroxide, and ammonium hydroxide. Preferably, the strong base is sodium or potassium hydroxide, more preferentially sodium hydroxide.

Preferably, the base used for the basic treatment is in the form of an aqueous basic solution.

In this case, the molar concentration of the base in aqueous solution is advantageously comprised between 0.1 and 5 $mol \cdot L^{-1}$, preferably comprised between 0.5 and 2 $mol \cdot L^{-1}$, still more preferentially equal to 1 $mol \cdot L^{-1}$ (for example molar caustic soda).

Preferably, the concentration of the base is adjusted so as to obtain a ratio of base by dry weight in g:solid residue by dry weight in g:water by weight in g comprised between 0.1:0.45:2 and 0.8:0.45:15, more preferentially comprised between 0.3:0.45:8 and 0.7:0.45:12, such as for example approximately 0.36:0.45:9.23.

This step of basic treatment of the solid residue is described more fully in step 4 of the detailed method for obtaining chitin and/or chitosan according to the invention hereafter.

Advantageously, the step of basic treatment of the solid residue is followed by a step of recovering the chitin.

This step of recovering the chitin is described more fully in step 5 of the detailed method for obtaining chitin and/or chitosan according to the invention hereafter.

Optionally, the method for obtaining chitin and/or chitosan according to the invention moreover comprises a step of washing the chitin.

This optional step of washing the chitin is described more fully in step 6 of the detailed method for obtaining chitin and/or chitosan according to the invention hereafter.

Optionally, the method for obtaining chitin and/or chitosan according to the invention moreover comprises a step of drying the chitin.

This optional step of drying the chitin is described more fully in step 7 of the detailed method for obtaining chitin and/or chitosan according to the invention hereafter.

As the chitin can be sold in the form of powder, the method for obtaining chitin and/or chitosan according to the invention can optionally comprise a step of grinding the chitin.

This optional step of grinding the chitin is described more fully in step 8 of the detailed method for obtaining chitin and/or chitosan according to the invention hereafter.

The grinding step can also be performed in order to promote the deacetylation reaction, which makes it possible to prepare chitosan from chitin.

The deacetylation step, which is intended to convert the chitin to chitosan, is therefore only carried out if the desired product is chitosan.

This step of deacetylation of the chitin is described more fully in step 9 of the detailed method for obtaining chitin and/or chitosan according to the invention hereafter.

Advantageously, the step of deacetylation of the chitin is followed by a step of recovering the chitosan.

This step of recovering the chitosan is described more fully in step 10 of the detailed method for obtaining chitin and/or chitosan according to the invention hereafter.

Optionally, the method for obtaining chitin and/or chitosan according to the invention moreover comprises a step of washing the chitosan.

This optional step of washing the chitosan is described more fully in step 11 of the detailed method for obtaining chitin and/or chitosan according to the invention hereafter.

Optionally, the method for obtaining chitin and/or chitosan according to the invention moreover comprises a step of drying the chitosan.

This optional step of drying the chitosan is described more fully in step 12 of the detailed method for obtaining chitin and/or chitosan according to the invention hereafter.

It will be noted that steps 6 to 8, 11 and 12 mentioned above, and described more fully in the detailed method for obtaining chitin and/or chitosan according to the invention hereafter, are optional. However, the method for obtaining chitin and/or chitosan according to the invention advantageously comprises one or more of these steps, preferably all of these steps.

It will additionally be noted that the features of steps 1 to 12 of the detailed method for obtaining chitin and/or chitosan according to the invention, which are described hereafter, are not limited to a use in said detailed method, but apply to all of the embodiments of the method for obtaining chitin and/or chitosan according to the invention described in the present application, independently of the number of steps provided in these embodiments.

These features also apply to a particular method for obtaining chitin and to a particular method for obtaining chitosan according to the invention, described hereafter.

The invention is therefore aimed more particularly at a particular method for obtaining chitin, from insects, comprising the following steps:
  killing of the insects,
  separation of the cuticles from the soft part of the insects,
  enzymatic hydrolysis of the cuticles by a protease, in order to obtain a solid residue,
  basic treatment of the solid residue, and
  recovery of the chitin.

This method therefore comprises steps 1 to 5 of the detailed method for obtaining chitin and/or chitosan hereafter and advantageously one or more of the optional steps 6 to 8 of this detailed method.

The invention also relates to the chitin that can be obtained using the method for obtaining chitin and/or chitosan according to the invention, or using the particular method for obtaining chitin according to the invention.

The invention is therefore also aimed at a particular method for obtaining chitosan, from insects, comprising the following steps:
  killing of the insects,
  separation of the cuticles from the soft part of the insects,
  enzymatic hydrolysis of the cuticles by a protease, in order to obtain a solid residue,
  basic treatment of the solid residue,
  recovery of the chitin,
  deacetylation of the chitin, and
  recovery of the chitosan.

This method therefore comprises steps 1 to 5, 9 and 10 of the detailed method for obtaining chitin and/or chitosan hereafter and advantageously one or more of the optional steps 6 to 8, 11 and 12 of this detailed method.

The invention also relates to the chitosan that can be obtained using the method for obtaining chitin and/or chitosan according to the invention, or using the particular method for obtaining chitosan according to the invention.

The chitin and/or the chitosan according to the invention and the chitin and/or chitosan that can be obtained using a method according to the invention can advantageously be used in various applications:
  in cosmetic, pharmaceutical, nutraceutical or dietary compositions,
  as biomaterials for treating burns, as a second skin, in order to make corneal dressings or surgical threads,
  as filtering, texturing, flocculating and/or adsorbing agent in particular for water filtration and water pollution control.

Detailed Method for Obtaining Chitin and/or Chitosan According to the Invention

•Step 1: Killing of the Insects

This killing step 1 can advantageously be performed by thermal shock, such as by scalding or by blanching. This step 1 makes it possible to kill the insects while lowering the microbial load (reducing the risk of alteration and health risk) and inactivating the internal enzymes of the insects that can trigger autolysis, and thus a rapid browning of them.

For the scalding, the insects, preferably the larvae, are thus scalded in water for 2 to 20 minutes, preferentially 5 to 15 minutes. Preferably, the water is at a temperature comprised between 87 and 100° C., preferentially 92 and 95° C.

The quantity of water introduced during the scalding is determined as follows: the ratio of the volume of water in ml to the weight in g of insect is preferably comprised between 0.3 and 10, more preferentially between 0.5 and 5, still more preferentially between 0.7 and 3, still more preferentially of the order of 1.

For the blanching, the insects, preferably the larvae, are blanched in water or in steam (steam nozzles or bed) at a temperature comprised between 8° and 105° C., preferably between 87 and 105° C., more preferentially between 95 and 100° C., still more preferentially 98° C. or even in water at a temperature comprised between 9° and 100° C., preferentially between 92 and 95° C. (through spray nozzles) or in a mixed mode (water+steam) at a temperature comprised between 80 and 130° C., preferably between 9° and 120° C., more preferentially between 95 and 105° C., still more preferentially 98° C. If the insects are blanched only in steam, the blanching is advantageously carried out in forced steaming blanching machines. The residence time in the blanching chamber is comprised between 5 seconds and 15 minutes, preferentially between 1 and 7 minutes.

Advantageously, following killing step 1, the insects are directly used to carry out step 2 of separating the cuticles from the soft part of the insects, i.e. the insects are not subjected to any treatment, such as a grinding, freezing or dehydration, between step 1 and step 2.

According to a preferred embodiment, the insects are coleopterans and in particular *Tenebrio molitor*.

•Step 2: Separation of the Cuticles from the Soft Part of the Insects

The objective of step 2 is to separate the cuticles from the soft part of the insects.

The separation of the cuticles from the soft part of the insects can be performed using any suitable type of separator.

According to a first embodiment, the separation of the cuticles from the soft part is carried out using a belt separator.

By "belt separator" is meant a device that makes it possible to separate the solid part from the soft part of a product, and which comprises a squeezing belt (or belt press) and a perforated drum.

By way of example, a belt separator can comprise a squeezing belt and a perforated drum, wherein the squeezing belt surrounds at least part of the perforated drum.

The squeezing belt allows insects to be conveyed to and applied against the perforated drum so as to make the soft part of the insects pass, by pressure, through the perforations of the drum, while the solid part of the insects (cuticles) remains outside the drum.

The cuticles can then be recovered using a scraper blade.

By way of example, there may be mentioned the belt separators from the Baader company, such as the belt separators 601 to 607 ("soft separator 601 to 607"), or else the SEPAmatic® belt separators from BFD Corporation (range 410 to 4000V).

Advantageously, the diameter of the perforations of the drum is comprised between 0.5 and 3 mm, preferably between 1 and 2 mm.

With regard to the pressure, a person skilled in the art is capable of determining the pressure to be exerted to make it possible to separate the cuticles from the soft part of the insects.

According to a second embodiment, the separation of the cuticles from the soft part is carried out using a filter press.

A filter press is composed of filter cloths, and allows a separation according to the principle of pressure filtration.

Advantageously, the filter press used in the method for obtaining chitin and/or chitosan according to the invention is a belt filter press.

A belt filter press comprises two perforated squeezing belts (also called "filter cloths"). The insects are placed between the two perforated squeezing belts so as to make the soft part of the insects pass, by pressure, through the perforations of the squeezing belts, while the solid part of the insects remains between the two perforated squeezing belts.

A person skilled in the art is capable of determining the diameter of the perforations of the squeezing belts as well as the pressure to be exerted to make it possible to separate the cuticles from the soft part of the insects.

By way of example, there may be mentioned the belt filter press (or "belt press") from the Flottweg company, or also the belt filter presses from the ATR Creations company.

This step of separating the insects differs from conventional pressing that can be carried out for example with a single or twin screw press in that it makes it possible to (cleanly) separate the soft part and the cuticles of the insects and not to separate a juice from a solid fraction.

Advantageously, the separation of the cuticles from the soft part of the insects is performed using a belt separator.

The cuticles obtained in step 2 contain between 10 and 30%, preferably between 15 and 25%, by weight chitin, relative to the total dry weight of cuticles.

The determination of the level of chitin is performed by extraction therefrom. By way of example, a method for determining the chitin content that can be used is the AOAC 991.43 method.

According to a preferred embodiment, the separation of the cuticles from the soft part of coleopterans and in particular of *Tenebrio molitor* is performed using a belt separator.

•Step 3: Enzymatic Hydrolysis of the Cuticles by a Protease

The enzymatic hydrolysis is performed by a protease or peptidase. In the present application, the names or suffixes "peptidase" and "protease" are used equally to denote an enzyme that lyses a peptide bond of proteins.

Advantageously, the enzymatic hydrolysis is performed for a duration comprised between 3 and 10 hours, preferentially comprised between 4 and 8 hours, such as for example of the order of 6 hours.

Preferably, the enzymatic hydrolysis is carried out at a temperature comprised between 4° and 80° C., preferentially comprised between 5° and 70° C., such as for example approximately 60° C.

Advantageously, the enzymatic hydrolysis is carried out at a pH comprised between 6 and 8, preferentially between 6.5 and 7.5.

The enzymatic hydrolysis can be carried out with a single protease or alternatively with a mixture of enzymes containing at least one protease, more preferentially a mixture of enzymes containing several proteases, such as a mixture containing an endoprotease and an exoprotease, or a protease and a polysaccharase.

Preferably, the protease is chosen from the group constituted by aminopeptidases, metallocarboxypeptidases, serine endopeptidases, cysteine endopeptidases, aspartic endopeptidases, metalloendopeptidases, more preferentially the protease is chosen from serine endopeptidases, such as, for example, Alcalase 2.5 L PF or Prolyve NP.

| Enzyme(s) | Class | EC number | Supplier |
|---|---|---|---|
| Flavourzyme | Aminopeptidases | EC 3.4.11.1 | Novozyme |
| Fungal protease 500 | | EC 3.4.11.1 | Bio-Cat |
| FoodPro PXT | Serine endopeptidases | EC 3.4.21 | Dupont Danisco |
| Chymotrypsin | | EC 3.4.21.1 | Novozyme |
| Protamex | | EC 3.4.21 | Novozyme |
| Trypsin | | EC 3.4.21.4 | Novozyme |
| Prolyve NP | | EC 3.4.21.63 | Lyven |
| Novozyme 37071 | | EC 3.4.21.62 | Novozyme |
| Alcalase 2.5L PF | | EC 3.4.21.62 | Novozyme |
| Papain | Cysteine endopeptidases | EC 3.4.22.2 | Bio-Cat |
| Bromelain (ananas) | | EC 3.4.22.32 | Bio-Cat |
| Izyme BA | Aspartic endopeptidases | EC 3.4.23 | Novozyme |
| Pepsin | | EC 3.4.23.1 | Sigma Aldrich |
| Neutral protease | Metalloendopeptidases | EC 3.4.24.28 | Bio-Cat |
| FoodPro PNL | | EC 3.4.24.28 | Dupont Danisco |
| Neutrase | | EC 3.4.24 | Novozyme |

| Enzyme(s) | Class | EC number | Supplier |
|---|---|---|---|
| FoodPro PAL | Acid fungal endopeptidase | EC 3.4.21 | Dupont Danisco |
| Pancrealyve | Exo & endo peptidase (cocktail of proteases + amylases) | n.a.* | Lyven |
| Sumizyme LP | Enzyme cocktail | EC 3.4.11.1 EC 3.4.21.63 EC 3.4.23.18 | Takabio - Shin Nihon |

* n.a.: not applicable

The enzyme or the mixture of enzymes is introduced in a quantity ranging from 0.2 to 15% by weight, preferably from 0.2 to 10% by weight, more preferentially from 1 to 8% by weight, still more preferentially from 3 to 7% by weight, relative to the weight of (wet) cuticles subjected to the enzymatic hydrolysis.

In terms of enzymatic activity, the quantity of enzyme or mixture of enzymes introduced is equivalent to an activity comprised between 2000 and 5000 SAPU ("Spectrophotometric Acid Protease Unit"), preferably comprised between 3000 and 4000 SAPU, per 100 g by wet weight, with a moisture content of from 30 to 70%, of substrate to be converted, i.e. of insect cuticles.

It is usual to express the enzymatic activity of a protease in SAPU.

This enzymatic activity is measured on the principle of measuring the release of tyrosine at 275 nm during hydrolysis of casein by a proteolytic enzyme (Valley research SAPU Assay method, by Karen PRATT).

$$\frac{SAPU}{g} = \frac{(\Delta A - i) \times 11}{m \times 30 \times C \times 1}$$

SAPU/g=a spectrophotometric protease unit
ΔA=correlated absorbance
i=y-intercept
11=final reaction volume
M=leading coefficient of the calibration curve
30=reaction time (in minutes)
C=concentration of the enzyme (g/mL) in the enzyme solution added
1=1 mL volume of the enzyme solution added The enzymatic activity can also be expressed using the specific activity of an enzyme.

The specific activity of an enzyme is the catalytic activity expressed in International Unit (IU) per unit of mass of enzyme (for example: IU/g enzyme).

Advantageously, the concentration of the enzyme or of the mixture of enzymes used is comprised between 100 and 250 IU per gram of dry matter of cuticles, preferably between 120 and 180 IU per gram of dry matter of cuticles, more preferentially between 120 and 150 IU per gram of dry matter of cuticles.

Advantageously, the enzymatic hydrolysis step is performed in the presence of water, such as fresh water.

The quantity of water used during the enzymatic hydrolysis is determined as follows: the ratio of the volume of water in L to the weight in g of wet cuticles is preferably comprised between 0.005 and 5, more preferentially between 0.01 and 5, such as for example approximately 0.01, or alternatively between 0.05 and 2, or between 0.1 and 1.

The enzymatic hydrolysis step is advantageously carried out under stirring.

According to a preferred embodiment, the enzymatic hydrolysis step is performed for 5 to 7 h, such as for example approximately 6 hours, at a temperature of from 50 to 70° C., such as for example approximately 60° C., and the enzyme is a serine endopeptidase, such as for example Alcalase 2.5 L PF. Preferably, the enzyme is introduced in a concentration comprised between 120 and 150 IU, such as for example of the order of 120 IU per gram of dry matter of cuticles. Preferably, the quantity of water used during this enzymatic hydrolysis step is of the order of 0.01 L water per g of wet cuticles.

At the end of the enzymatic hydrolysis reaction of the cuticles, the reaction medium is then separated, in order to recover a solid residue comprising chitin and a hydrolysate.

The separation step can be carried out using any suitable separation method. These methods are known to a person skilled in the art.

By way of example, it is possible to use a juicer, such as those sold by the Angel® company.

The solid residue recovered is advantageously homogenized, for example by mixing.

•Step 4: Basic Treatment of the Solid Residue

In step 4, the solid residue recovered at the end of step 3 is subjected to a basic treatment, i.e. it is brought into contact with a base (or basic agent).

Advantageously, the basic treatment is carried out using a strong base.

Advantageously, the strong base is chosen from sodium hydroxide or caustic soda, potassium hydroxide, and ammonium hydroxide. Preferably, the strong base is sodium or potassium hydroxide, more preferentially sodium hydroxide.

Preferably, the base used for the basic treatment is in the form of an aqueous basic solution.

In this case, the molar concentration of the base in aqueous solution is advantageously comprised between 0.1 and 5 mol·L$^{-1}$, preferably comprised between 0.5 and 2 mol·L$^{-1}$, still more preferentially equal to 1 mol·L$^{-1}$ (for example molar caustic soda).

Preferably, the concentration of the base is adjusted so as to obtain a ratio of base by dry weight in g:to solid residue by dry weight in g:water by weight in g comprised between 0.1:0.45:2 and 0.8:0.45:15, more preferentially comprised between 0.3:0.45:8 and 0.7:0.45:12, such as for example approximately 0.36:0.45:9.23.

The basic treatment is advantageously carried out for a duration comprised between 5 and 60 hours, preferably for a duration comprised between 5 and 50 hours, such as for example 48 hours.

The duration of the basic treatment can advantageously be adapted according to the properties of the chitin that it is desired to obtain, such as its whiteness (white colour).

The duration of the basic treatment can be less than 40 hours, or even less than 30 hours, such as for example 24 hours.

Advantageously, the basic treatment is carried out at a temperature comprised between 6° and 100° C., preferably comprised between 8° and 100° C., more preferentially approximately 90° C.

Therefore, the reaction medium can, for example, be heated using an oil bath, a heat exchanger or a double-envelope heating system, so as to reach the desired temperature.

The step of basic treatment is advantageously carried out under stirring.

According to a first preferred embodiment, the step of basic treatment is carried out using sodium hydroxide in the form of an aqueous basic solution. Preferably, the concentration of the sodium hydroxide in aqueous solution is equal to 1 mol·L$^{-1}$. Preferably, the ratio of sodium hydroxide by dry weight in g:solid residue by dry weight in g:water by weight in g is of the order of 1:1:25. Preferably, the duration of this basic treatment is approximately 48 hours. Preferably, this basic treatment is carried out at a temperature of approximately 90° C.

According to a second preferred embodiment, the step of basic treatment is carried out using potassium hydroxide in the form of an aqueous basic solution. Preferably, the concentration of the potassium hydroxide in aqueous solution is equal to 1 mol·L$^{-1}$. Preferably, the ratio of potassium hydroxide by dry weight in g:solid residue by dry weight in g:water by weight in g is of the order of 1.4:1:25. Preferably, the duration of this basic treatment is approximately 48 hours. Preferably, this basic treatment is carried out at a temperature of approximately 90° C.

•Step 5: Recovery of the Chitin

Step 5 of recovering the chitin, from the reaction medium obtained at the end of step 4, can be carried out using any suitable recovery method. These methods are known to a person skilled in the art.

By way of example, there may be mentioned filtration, centrifugation and decantation.

Advantageously, the recovery of the chitin is carried out by filtration.

•(Optional) Step 6: Washing of the Chitin

The chitin recovered at the end of step 5 is then optionally washed.

Step 6 of washing the chitin is advantageously carried out using tap water, preferably tepid, i.e. the temperature of which is comprised between 15 and 60° C.

Preferably, the washing is carried out until neutralization of the pH.

•(Optional) Step 7: Drying of the Chitin

The chitin is then optionally dried.

Preferably, the drying step is carried out at a temperature comprised between 4° and 105° C., preferably at approximately 60° C.

The drying step is carried out for a duration comprised between 10 and 80 hours, preferably for approximately 24 hours.

Advantageously, the drying is carried out using a drying oven, such as the FED 115 or FP53 model from the Binder® company.

In order to prepare chitosan from chitin, the following steps can be carried out in addition:

•(Optional) Step 8: Grinding of the Chitin

The chitin obtained at the end of step 5, 6 or 7 is then optionally ground, for example in an ultra centrifugal grinder with a sieve.

The production of chitosan from chitin, by deacetylation reaction, largely depends on the size of the chitin particles. Thus, a very fine grinding of the chitin before deacetylation makes it possible to significantly increase the yields and the speed of the deacetylation reaction, as is illustrated in Table 1 below:

TABLE 1

Efficiency of the deacetylation depending on the prior grinding of the chitin

| | Grinding 30 s | Grinding 45 s | Grinding 60 s | Grinding 120 s |
|---|---|---|---|---|
| 50% of the particles | <174 µm | <117 µm | <95 µm | <67 µm |
| 90% of the particles | <310 µm | <244 µm | <157 µm | <159 µm |
| DA* | 99% | 90% | 85% | 80% |

*Measurement of the Degree of Acetylation DA

The conditions of the deacetylation performed in the test reported in Table 1 are as follows: 4 hours of reaction, 100° C., NaOH in aqueous solution at 30% by volume, in a ratio of estimated chitin to NaOH solution equal to 1:20.

As a result, the chitin is preferentially ground to a particle size smaller than 300 µm, such as a size smaller than 260 µm, or smaller than 200 µm, or also smaller than 160 µm.

•Step 9: Deacetylation of the Chitin

This step is only carried out in the case where it is desired to obtain chitosan.

The chitin is then placed in a reactor, where a base is added.

Advantageously, the deacetylation of the chitin is carried out using a strong base.

Advantageously, the strong base is chosen from sodium hydroxide or caustic soda, potassium hydroxide, and ammonium hydroxide. Preferably, the strong base is sodium or potassium hydroxide, more preferentially sodium hydroxide.

Preferably, the base used for the basic treatment is in the form of an aqueous basic solution, preferably a concentrated aqueous basic solution.

In this case, the molar concentration of the base in aqueous solution is advantageously comprised between 4 and 25 mol·L$^{-1}$, preferably comprised between 6 and 22 mol·L$^{-1}$, more preferentially comprised between 8 and 19 mol·L$^{-1}$, still more preferentially comprised between 10 and 19 mol·L$^{-1}$, still more preferentially comprised between 12.5 and 19 mol·L$^{-1}$.

Preferably, the concentration of the base is adjusted so as to obtain a ratio of base by dry weight in g:chitin by dry weight in g:water by weight in g comprised between 18:1:35 and 55:1:55, such as for example comprised between 18:1:35 and 30:1:55, or approximately 24:1:45, more preferentially approximately 38:1:50. The most preferred values are in particular those to be used when sodium hydroxide is used.

Preferably, the deacetylation is carried out for 1 to 24 hours and preferentially 2 to 18 hours.

Advantageously, this deacetylation is carried out in two runs, with an intermediate step of neutralizing the pH. For example, the deacetylation can be carried out in two runs of two hours, i.e. for 4 hours, with an intermediate step of neutralizing the pH in between.

The deacetylation temperature is advantageously between 8° and 150° C., preferably between 9° and 120° C. and more preferentially at 100° C.

•Step 10: Recovery of the Chitosan

Step 10 of recovering the chitosan, from the reaction medium obtained at the end of step 9, can be carried out using any suitable recovery method. These methods are known to a person skilled in the art.

By way of example, there may be mentioned filtration, centrifugation and decantation.

Advantageously, the recovery of the chitosan is carried out by filtration.

In the case where step 8 of grinding the chitin is carried out, the chitosan recovered is in the form of powder.

The chitosan can then be subjected to any operation known to a person skilled in the art that makes it possible to functionalize it, in particular by the addition of radicals (carboxylation, hydroxylation, etc.).

•(Optional) Step 11: Washing

The chitosan recovered at the end of step 10 is then optionally washed.

Step 11 of washing the chitosan is advantageously carried out using tap water. Preferably, this water has a temperature comprised between 15 and 60° C.

Preferably, the washing is carried out until neutralization of the pH.

•(Optional) Step 12: Drying

The chitosan, which can be in the form of powder, is then optionally dried between 3° and 80° C., advantageously between 5° and 70° C., preferably at approximately 60° C., in order to obtain chitosan or a chitosan powder having a dry matter content greater than 85%, more particularly greater than 90%.

The drying step is carried out for a duration comprised between 10 and 80 hours, preferably for approximately 24 hours.

Advantageously, the drying is carried out using a drying oven, such as the FED 115 or FP53 model from the Binder® company.

The invention will be better understood in the light of the following examples, which are given by way of illustration.

EXAMPLE 1: METHOD FOR OBTAINING CHITIN ACCORDING TO THE INVENTION

I. Materials and Methods

Larvae of *Tenebrio molitor* were used. On receipt of the larvae, the latter can be stored at 4° C. for 0 to 15 days in their rearing trays before being killed, without major degradation. The weight of the larvae (age) used is variable and as a result their composition can vary, as is illustrated in Table 2 below:

TABLE 2

Biochemical composition of the larvae of *Tenebrio molitor* according to their weight.

| Biomass (insects) | mg | 23 | 35 | 58 | 80 | 108 | 154 |
|---|---|---|---|---|---|---|---|
| Dry matter | %* | 34 | 34 | 34.2 | 37.9 | 39.6 | 39.5 |
| Ash | %* | 1.59 | 1.52 | 1.6 | 1.75 | 1.67 | 1.43 |
| Crude proteins | %* | 22.6 | 22.2 | 22 | 23.2 | 23.1 | 23.2 |
| Lipids | %* | 6.62 | 6.88 | 7.98 | 10.3 | 10.9 | 11.7 |

*The % are expressed in dry weight relative to the wet weight of larvae.

•Step 1: Killing of the Insects

The living larvae (+4° C. to +25° C.) are conveyed, in a layer with a thickness comprised between 2 and 10 cm, on a perforated conveyor belt (1 mm) to a blanching chamber. The insects are thus blanched in steam (steam nozzles or bed) at 98° C. under forced ventilation or else in water at 92-95° C. (spray nozzles) or in a mixed mode (water+steam). The residence time in the blanching chamber is comprised between 5 seconds and 15 minutes, ideally 5 minutes.

The temperature of the larvae after blanching is comprised between 75° C. and 98° C.

•Step 2: Separation of the Soft Part from the Cuticles of the Insects

The larvae, once blanched, are conveyed to the feed hopper of a belt separator, in order to separate the cuticles from the soft part of the larvae.

Advantageously, the separation is performed immediately after killing, such that the larvae do not have time to cool to ambient temperature.

The belt separator used is a belt separator 601 from the Baader company.

The diameter of the perforations of the drum is 1.3 mm.

The soft part of the insects is recovered in a tank.

The cuticles are recovered using a scraper blade.

The percentage of dry matter in the cuticles is approximately 35-45%.

•Step 3: Enzymatic Hydrolysis of the Cuticles by a Protease 160.015±0.007 g wet cuticles obtained in step 2 (Dry Matter=38±5%), 8 g Prolyve® NP (5% of the mass of wet cuticles) and 1.6 L±0.02 L hot water are placed in a 2-L three-neck flask equipped with a condenser and a stirrer (Heidolph® RZR1). The medium is heated with a bain marie to a temperature of 60±2° C. for 6 hours. Then, the temperature is brought to 80° C. for 15 min. The reaction medium is then separated using a juicer (Angelia 7500). Throughout the reaction, the reaction medium is subjected to a stirring of 280 rpm. The pH is comprised between 6 and 8, preferably between 6.5 and 7.5. The specific activity of Prolyve® NP is 1132.1 IU/g enzyme. 8 g Prolyve® NP, i.e. 9056.8 IU, is used per 160.015±0.007 g of wet cuticles (Dry Matter=38±5%). The concentration of the enzyme is therefore approximately 149 IU/g of dry matter of cuticles.

58±2 g of solid residue is obtained, and a hydrolysate. The solid residue is mixed in order to be homogeneous, weighed, then placed in a refrigerator overnight. The hydrolysate is lyophilized.

•Step 4: Basic Treatment of the Solid Residue

The solid residue obtained in step 3 (Dry Matter=44±16%) and 512.05±0.02 mL aqueous sodium hydroxide solution with a concentration equal to 1 mol·L$^{-1}$ are placed in a 2-L three-neck flask equipped with a condenser and a mechanical stirrer (Heidolph® RZR1). The medium is heated with an oil bath to a temperature of 90±2° C. for 24 hours.

Approximately 0.02 L aqueous sodium hydroxide solution per gram of dry matter of solid residue is therefore used.

The ratio of base by dry weight in g:solid residue by dry weight in g:water by weight in g is approximately equal to 0.36:0.45:9.23.

•Step 5: Recovery of the Chitin

The reaction medium obtained at the end of step 4 is then filtered (SEFAR MEDIFABR 03-60/42 filter) so as to recover the chitin.

•(Optional) Step 6: Washing of the Chitin

The chitin recovered at the end of step 5 is then rinsed with tepid tap water until neutralization of the pH.

•(Optional) Step 7: Drying of the Chitin

The chitin is then dried for 24 hours, at 60° C., in a drying oven (Binder®, FP53 model).

9.6±0.2 g chitin is thus obtained.

II. Analysis Methods

Measurement of the Dry Matter and of the Moisture Content

The percentage of dry matter and the moisture content are calculated as follows.

2 g chitin are weighed into cups, introduced into a drying oven (Binder®, FED 115 model) and dried at 105° C. for 24 h (or until completely dry).

The percentage of dry matter is obtained by making the ratio of the dry mass of chitin after drying to the mass of chitin before drying.

The moisture content is obtained by subtracting the percentage of dry matter from the value of 100%.

This measurement method can also be used to measure the percentage of dry matter and the moisture content of the cuticles.

Measurement of the Ash Content

The ash content was determined according to the method from NF V18-101 standard.

Measurement of the Crude Protein Content

The protein content is obtained using the Dumas method, with the conversion coefficient of 6.25, adapted from the NF EN ISO 16634-1 standard.

Measurement of the Lipid or Fat Content

The lipid content is obtained using a method adapted from the EC 152/2009 regulation—Method B-SN.

Amino Acid Content and Relative Abundance

The amino acid content of the chitin according to the invention is preferably determined according to the NF EN ISO 13904 method or a method adapted from the EC 152/2009 regulation of 27-01-2009-SN (these two methods being equivalent) for tryptophan, and according to the NF EN ISO 13903 method or a method from the EC 152/2009 regulation of 27-01-2009-SN for the other amino acids (these two methods being equivalent).

The relative abundance was calculated by relating each amino acid content to the total amino acid content.

Total Amino Acid Content

The total amino acid content was determined by adding up the individual values obtained for each amino acid, including tryptophan.

Purity by Difference

For this measurement, the known impurity contents (amino acids, lipids and ash) were subtracted from the absolute purity value (100%) in order to obtain the value of the estimated purity by difference. For example, a sample which contains 30% amino acids, 10% lipids and 1% ash is consequently attributed a purity by difference of 100−30−10−1=59%.

Molecular Mass of the Chitin

The molecular mass was determined according to a falling ball viscosity measurement method based on the one described in the following publication: "Pacheco et al.; *Structural characterization of chitin and chitosan obtained by biological and chemical methods; Biomacromolecules;* 12, 3285-3290, 2011".

In particular, the method for determining the molecular mass of the chitin is based on viscosity measurements of diluted solutions of chitin. The dilutions are carried out in dimethylacetamide containing 5% lithium chloride (DMAc-LiCl 5%). In fact, the polymers in solution increase the viscosity of a solvent. The viscosity of the polymer in solution depends on its concentration and its molecular mass. The relationship is defined by the Mark-Houwink-Sakurada equation:

$$[\eta] = K M^\alpha$$

with $[\eta]$: the intrinsic viscosity, M: the molecular mass, K and a specific constants of a solvent/polymer system at a given temperature.

The values for chitin dissolved in the solvent DMAc-LiCl 5% at 25° C. are: K=0.24 mL·g$^{-1}$ and α=0.69 (Pacheco et al.; 2011).

The intrinsic viscosity corresponds to the specific viscosity when the concentration of the polymer tends towards zero.

$$[\eta] = \lim_{c \to 0} \left( \frac{\eta \, sp}{c} \right)$$

In order to measure the specific viscosity of the chitin, five solutions with weak concentrations are prepared in DMAc-LiCl 5%. The flow times of the solvent alone (to) and of the solutions (t) with different concentrations are measured using a falling ball micro viscometer in order to calculate the relative viscosity ($\eta_r$). From the relative viscosity ($\eta_r$), it is necessary to calculate the specific ($\eta_{sp}$), reduced ($\eta_{red}$) and inherent ($\eta_{inh}$) viscosities of each concentration of chitin.

$$\eta_{sp} = \eta_r - 1; \eta_{red} = \frac{\eta \, sp}{c}; \eta_{inh} = \frac{\ln(\eta r)}{c}$$

The intrinsic viscosity is then calculated by plotting the curves "concentration vs. reduced viscosity" (positive slope) and "concentration vs. inherent viscosity" (negative slope). Each of these curves is extrapolated from zero concentration. The y-intercept corresponds to the intrinsic viscosity. Similar results are expected from the two curves. Finally, in order to determine the molecular mass of the chitin, the Mark-Houwink-Sakurada equation is applied.

III. Results

The properties of the chitin obtained are given in Table 3 below.

TABLE 3

| Properties of the chitin obtained in Example 1 | |
|---|---|
| Ash (g/100 g DM*) | 1.11 +/− 0.25 |
| Fats (g/100 g DM*) | 0 +/− 0.00 |
| Total aa content (g/100 g DM*) | 0.72 +/− 0.08 |
| Purity by difference (%) | 98.16 +/− 0.33 |
| Molecular mass (kg · mol$^{-1}$) | 642 +/− 125 |

*DM: dry matter

The relative abundance of amino acids in the chitin obtained is given in Table 4 below. It is expressed in %.

TABLE 4

| Relative abundance of amino acids in the chitin obtained in Example 1 | |
|---|---|
| Threonine (Thr) | 0.00 |
| Serine (Ser) | 0.00 |
| Proline (Pro) | 0.00 |
| Glycine (Gly) | 0.00 |
| Glutamic acid (Glu) | 0.00 |
| Alanine (Ala) | 0.00 |
| Cysteine (Cys) | 6.88 |
| Valine (Val) | 16.51 |
| Methionine (Met) | 0.00 |
| Isoleucine (Ile) | 0.00 |
| Aspartic acid (Asp) | 0.00 |
| Leucine (Leu) | 0.00 |

TABLE 4-continued

Relative abundance of amino acids
in the chitin obtained in Example 1

| | |
|---|---|
| Tyrosine (Tyr) | 0.00 |
| Phenylalanine (Phe) | 0.00 |
| Histidine (His) | 46.78 |
| Lysine (Lys) | 29.58 |
| Arginine (Arg) | 0.00 |
| Tryptophan (Trp) | 0.25 |
| Total | 100.00 |

Three amino acids appear to be particularly resistant to the method, namely valine, histidine and lysine. In fact they represent more than 93% of the residual amino acids.

EXAMPLE 2: METHOD FOR OBTAINING CHITOSAN ACCORDING TO THE INVENTION

In order to prepare chitosan, the chitin resulting from step 5, 6 or 7 of Example 1 is used.
•(Optional) Step 8: Grinding of the Chitin
The chitin was ground in an ultra centrifugal grinding mill with a sieve to a size of 250 μm.
•Step 9: Deacetylation of the Chitin
The chitin is then placed in a reactor, where a concentrated caustic soda solution is added. The sodium hydroxide in aqueous solution at a level of 50% (i.e. a concentration of sodium hydroxide in aqueous solution of 12.5 mol/L) is added in a ratio of weight in g ground chitin/volume in mL sodium hydroxide in aqueous solution equal to 1:50. The tank is then heated to a temperature of 100° C. The deacetylation reaction is carried out for 2 hours twice, with an intermediate step of neutralization of the pH.
•Step 10: Recovery of the Chitosan
The reaction medium obtained at the end of step 9 is then filtered (SEFAR MEDIFAB® 03-60/42 filter) so as to recover the chitosan.
•(Optional) Step 11: Washing
The chitosan recovered at the end of step 10 is then rinsed with tepid tap water until neutralization of the pH.
Powdered chitosan is thus obtained.
The chitosan obtained has a purity by difference greater than 98%.
The molecular mass of the chitosan obtained is equal to $307 +/- 60 \text{ kg} \cdot \text{mol}^{-1}$.
•(Optional) Step 12: Drying
The chitosan powder is then dried at 60° C. in order to obtain a powder having a dry matter content greater than 85%.

EXAMPLE 3: COMPARATIVE METHOD FOR OBTAINING CHITIN

I. Materials and Methods

•Step 1: Killing of the Insects
This step is identical to the one in Example 1.
•Step 2: Separation of the Cuticles from the Soft Part of the Insects
This step is identical to the one in Example 1.
•Step 3: Basic Treatment of the Cuticles
90.02±0.02 g wet cuticles obtained in step 2 (Dry Matter=40.1±0.1%) and 1.80±0.02 L aqueous sodium hydroxide solution with a concentration equal to 1 mol·L$^{-1}$ are placed in a 2-L three-neck flask equipped with a condenser and a mechanical stirrer (Heidolph® RZR1). The medium is heated with an oil bath to a temperature of 90±2° C. for 48 hours. Throughout the reaction, the reaction medium is subjected to a stirring of 280 rpm.
Approximately 0.05 L aqueous sodium hydroxide solution per gram of dry matter of cuticles is therefore used.
The ratio of base by dry weight in g:cuticles by dry weight in g:water by weight in g is approximately equal to 0.9: 0.45:22 . . . .
•Step 4: Recovery of the Chitin
The reaction medium obtained at the end of step 3 is then filtered (SEFAR MEDIFAB® 03-60/42 filter) so as to recover the chitin.
•(Optional) Step 5: Washing of the Chitin
The chitin recovered at the end of step 4 is then rinsed with tepid tap water until neutralization of the pH.
•(Optional) Step 6: Drying of the Chitin
The chitin is then dried for 24 hours, at 60° C., in a drying oven (Binder®, FP53 model).
6.3±0.2 g chitin is thus obtained.

II. Results

The properties of the chitin obtained at the end of step 6 are given in Table 5 below.

TABLE 5

| Properties of the chitin obtained in Example 3 | |
|---|---|
| Ash (g/100 g DM*) | 1.71 +/- 0.11 |
| Fats (g/100 g DM*) | 0 +/- 0.00 |
| Total aa** content (g/100 g DM*) | 0.68 +/- 0.003 |
| Purity by difference (%) | 97.61 +/- 0.14 |

*DM: dry matter
**aa: amino acids

The relative abundance of amino acids in the chitin obtained is given in Table 6 below. It is expressed in %.

TABLE 6

Relative abundance of amino acids
in the chitin obtained in Example 3

| | |
|---|---|
| Threonine (Thr) | 0.00 |
| Serine (Ser) | 0.00 |
| Proline (Pro) | 0.00 |
| Glycine (Gly) | 0.00 |
| Glutamic acid (Glu) | 0.00 |
| Alanine (Ala) | 12.48 |
| Cysteine (Cys) | 5.87 |
| Valine (Val) | 8.07 |
| Methionine (Met) | 0.00 |
| Isoleucine (Ile) | 0.00 |
| Aspartic acid (Asp) | 0.00 |
| Leucine (Leu) | 0.00 |
| Tyrosine (Tyr) | 0.00 |
| Phenylalanine (Phe) | 0.00 |
| Histidine (His) | 44.77 |
| Lysine (Lys) | 28.62 |
| Arginine (Arg) | 0.00 |
| Tryptophan (Trp) | 0.19 |
| Total | 100.00 |

5 amino acids appear to be particularly resistant to the method, namely alanine, cysteine, valine, histidine and lysine. Histidine, lysine and alanine are the 3 most resistant amino acids. In fact they represent more than 85% of the residual amino acids.

EXAMPLE 4: OBTAINING CHITIN ACCORDING TO THE INVENTION FROM DIFFERENT INSECTS

Different insects were used in this example: *Tenebrio molitor, Pachnoda marginata, Zophobas morio* and *Galleria mellonella*.

The cuticles were obtained from the larval stage of the different insects according to steps 1 and 2 described in Example 1.

• Enzymatic Hydrolysis of the Cuticles by a Protease

The cuticles are then subjected to an enzymatic hydrolysis step under the following conditions:

$m_1$ g wet cuticles obtained in the preceding step (Dry Matter=$n_1$%), a quantity $q_1$ (g or mL) of protease and 1.6 L±0.02 L hot water are placed in a 2-L three-neck flask equipped with a condenser and a stirrer (Heidolph® RZR1), so that the protease concentration is approximately 140 IU/g dry cuticles. The medium is heated with a bain marie to a temperature of 60±2° C. for 6 hours. Then, the temperature is brought to 80° C. for 15 min. The reaction medium is then separated using a juicer (Angelia 7500). Throughout the reaction, the reaction medium is subjected to a stirring of 300 rpm. The pH is comprised between 6 and 8, preferably between 6.5 and 7.5.

$m_2$ g of solid residue is obtained, and a hydrolysate. The different experimental conditions are summarized in Table 7. The solid residue is mixed in order to be homogeneous, weighed, then placed in a refrigerator overnight. The hydrolysate is lyophilized.

TABLE 7

Experimental conditions of the different enzymatic hydrolyses as a function of the insects used

| Insect | Protease | Enzymatic activity (IU/g or mL of protease) | Quantity $q_1$ of protease | Initial mass $m_1$ of cuticles (g) | $n_1$ % dry matter | Mass $m'_1$ of dry cuticles (g) | Mass $m_2$ of solid residue obtained (g) |
|---|---|---|---|---|---|---|---|
| T. molitor | Prolyve | 1132.1 | 8 g | 160.02 ± 0.01 | 38.08 ± 0.00 | 60.93 ± 0.00 | 57.78 ± 2.33 |
| T. molitor | Food Pro PNL | 486.47 | 18.6 mL | 160.23 ± 0.25 | 39.50 ± 0.35 | 63.29 ± 0.59 | 66.97 ± 4.22 |
| T. molitor | Alcalase 2.5L PF | 952.24 | 9.5 mL | 160.42 ± 0.34 | 46.98 ± 0.37 | 75.36 ± 0.60 | 80.39 ± 13.75 |
| T. molitor | Prolyve | 1132.1 | 8 g | 160.19 ± 0.15 | 38.70 ± 0.00 | 61.99 ± 0.06 | 76.85 ± 33.56 |
| P. marginata | Prolyve | 1132.1 | 8 g | 196.23 ± 0.35 | 33.58 ± 3.38 | 65.89 ± 6.72 | 55.53 ± 6.21 |
| Z. morio | Prolyve | 1132.1 | 8 g | 138.98 ± 0.45 | 43.60 ± 3.00 | 60.58 ± 3.98 | 45.32 ± 2.48 |
| G. mellonella | Prolyve | 1132.1 | 8 g | 177.05 ± 0.24 | 38.42 ± 0.99 | 68.02 ± 1.76 | 46.02 ± 5.44 |

• Basic Treatment of the Solid Residue $M_2$ g solid residue obtained in the preceding step (Dry Matter=$n_2$%) and a volume $V_1$ ($V_1$=$m_2$*$n_2$*25 mL) of aqueous sodium hydroxide (or potassium hydroxide) solution with a concentration equal to 1.0 mol·L$^{-1}$ are placed in a 2-L three-neck flask equipped with a condenser and a mechanical stirrer (Heidolph® RZR1). The medium is heated with an oil bath to a temperature of 90±2° C. for 48 hours. Throughout the reaction, the reaction medium is subjected to a stirring of 300 rpm.

• Recovery, Washing and Drying of the Chitin

The chitin is recovered at the end of the step of basic treatment, washed, then dried under the conditions described in steps 5, 6 and 7 of Example 1 respectively.

The experimental conditions of the basic treatment for different insects are given in Table 8.

TABLE 8

Experimental conditions of the basic treatment of different insects

| Source of the solid residue | Base | Mass $m_2$ of solid residue (g) | $n_2$ % dry matter | Mass $m'_2$ of dry solid residue (g) | Volume $V_1$ of base (mL) | Ratio of dry base (g):dry solid residue (g):water (g) |
|---|---|---|---|---|---|---|
| T. molitor (Prolyve) | NaOH | 57.78 ± 2.33 | 43.62 ± 1.67 | 25.40 ± 10.64 | 635 ± 266 | 1:1:25 |
| T. molitor (Food Pro) | NaOH | 66.97 ± 4.22 | 30.50 ± 3.84 | 20.31 ± 1.48 | 508 ± 37 | 1:1:25 |
| T. molitor (Alcalase) | NaOH | 80.39 ± 13.75 | 28.45 ± 6.16 | 22.37 ± 2.75 | 559 ± 69 | 1:1:25 |
| T. molitor (Prolyve) | KOH | 76.85 ± 33.56 | 33.16 ± 16.60 | 24.51 ± 10.66 | 613 ± 267 | 1.4:1:25 |

TABLE 8-continued

Experimental conditions of the basic treatment of different insects

| Source of the solid residue | Base | Mass $m_2$ of solid residue (g) | $n_2$ % dry matter | Mass $m'_2$ of dry solid residue (g) | Volume $V_1$ of base (mL) | Ratio of dry base (g):dry solid residue (g):water (g) |
|---|---|---|---|---|---|---|
| P. marginata (Prolyve) | NaOH | 55.53 ± 6.21 | 29.61 ± 6.02 | 16.20 ± 1.68 | 405 ± 42 | 1:1:25 |
| Z. morio (Prolyve) | NaOH | 45.32 ± 2.48 | 34.24 ± 2.03 | 15.52 ± 1.30 | 388 ± 33 | 1:1:25 |
| G. mellonella (Prolyve) | NaOH | 46.02 ± 5.44 | 27.33 ± 4.99 | 12.46 ± 1.96 | 311 ± 49 | 1:1:25 |

A mass $m_3$ of chitin is collected. The yield is calculated as follows: $m_3/m'_1*100$ and the results are indicated in Table 9.

TABLE 9

Chitin extraction yields for different insects

| Source of the solid residue | Mass $m_3$ of chitin obtained (g) | Yield (%) |
|---|---|---|
| T. molitor (Prolyve + NaOH) | 9.62 ± 0.66 | 15.8 ± 1.1 |
| T. molitor (Food Pro + NaOH) | 12.35 ± 0.14 | 19.5 ± 0.4 |
| T. molitor (Alcalase + NaOH) | 14.36 ± 0.09 | 19.1 ± 0.1 |
| T. molitor (Prolyve + KOH) | 13.12 ± 0.30 | 21.2 ± 0.5 |
| P. marginata (Prolyve + NaOH) | 12.57 ± 0.48 | 19.2 ± 1.5 |
| Z. morio (Prolyve + NaOH) | 10.65 ± 1.00 | 17.6 ± 1.6 |
| G. mellonella (Prolyve + NaOH) | 10.89 ± 0.60 | 16.0 ± 1.0 |

The chitins are then analyzed according to the analysis methods indicated in point II of Example 1. The analysis results are given in Table 10, in which the ash, lipid and amino acid contents correspond to contents in grams per 100 g dry matter.

TABLE 10

Properties of the chitins obtained from different insects and different proteases

| Source of chitin | Molar mass (kDa) | Ash | Lipids | Amino acids | Purity by difference (%) |
|---|---|---|---|---|---|
| T. molitor (Prolyve + NaOH) | 666 ± 167 | 1.115 ± 0.25 | 0 ± 0.00 | 0.725 ± 0.08 | 98.16 ± 0.26 |
| T. molitor (Food Pro + NaOH) | 986 ± 110 | 1.36 ± 0.06 | 0.27 ± 0.01 | 0.605 ± 0.33 | 97.765 ± 0.34 |
| T. molitor (Alcalase + NaOH) | 929 ± 78 | 0.85 ± 0.07 | 0.285 ± 0.02 | 0.31 ± 0.01 | 98.555 ± 0.08 |
| T. molitor (Prolyve + KOH) | 895 ± 76 | 1.37 ± 0.05 | 0 ± 0.00 | 0.74 ± 0.02 | 97.89 ± 0.05 |
| P. marginata (Prolyve + NaOH) | 782 ± 105 | 1.105 ± 0.39 | 0.225 ± 0.08 | 0.32 ± 0.01 | 98.35 ± 0.40 |
| Z. morio (Prolyve + NaOH) | 693 ± 76 | 1.03 ± 0.31 | 0.28 ± 0.08 | 0.33 ± 0.20 | 98.36 ± 0.38 |
| G. mellonella (Prolyve + NaOH) | 498 ± 51 | 1.255 ± 0.13 | 0 ± 0.00 | 0.305 ± 0.01 | 98.44 ± 0.13 |

The method according to the invention makes it possible to obtain a chitin having a high purity, whatever the insect or the hydrolysis conditions (protease and base) used.

The relative abundance of amino acids in the chitins obtained is given in Table 11 below and is expressed in percent.

TABLE 11

Relative abundance of amino acids in the chitins obtained from different insects

| | T. molitor (Prolyve + NaOH) | T. molitor (Food Pro + NaOH) | T. molitor (Alcalase + NaOH) | T. molitor (Prolyve + KOH) | P. marginata (Prolyve + NaOH) | Z. morio (Prolyve + NaOH) | G. mellonella (Prolyve + NaOH) |
|---|---|---|---|---|---|---|---|
| threonine | 0.000 | 18.122 | 14.400 | 18.970 | 60.681 | 46.892 | 29.402 |
| serine | 0.000 | 3.295 | 0.000 | 0.000 | 0.000 | 0.000 | 0.000 |
| proline | 0.000 | 0.000 | 0.000 | 0.000 | 0.000 | 0.000 | 0.000 |
| glycine | 0.000 | 4.942 | 0.000 | 0.000 | 0.000 | 0.000 | 0.000 |
| glutamic acid | 0.000 | 9.061 | 22.400 | 10.840 | 10.892 | 15.126 | 0.000 |
| alanine | 0.000 | 4.119 | 0.000 | 0.000 | 0.000 | 0.000 | 0.000 |
| cysteine | 6.879 | 0.000 | 0.000 | 0.000 | 0.000 | 0.000 | 0.000 |
| valine | 16.510 | 0.000 | 0.000 | 0.000 | 0.000 | 13.614 | 0.000 |
| methionine | 0.000 | 0.000 | 0.000 | 0.000 | 0.000 | 0.000 | 0.000 |
| isoleucine | 0.000 | 0.000 | 0.000 | 29.133 | 0.000 | 0.000 | 0.000 |
| aspartic acid | 0.000 | 4.119 | 9.600 | 0.000 | 0.000 | 0.000 | 0.000 |
| leucine | 0.000 | 0.000 | 0.000 | 6.775 | 0.000 | 0.000 | 0.000 |
| tyrosine | 0.000 | 8.237 | 0.000 | 0.000 | 28.007 | 19.664 | 0.000 |
| phenylalanine | 0.000 | 4.119 | 0.000 | 4.743 | 0.000 | 0.000 | 6.534 |
| histidine | 46.777 | 4.942 | 0.000 | 2.710 | 0.000 | 4.538 | 0.000 |
| lysine | 29.580 | 38.715 | 52.800 | 26.423 | 0.000 | 0.000 | 63.705 |
| arginine | 0.000 | 0.000 | 0.000 | 0.000 | 0.000 | 0.000 | 0.000 |
| tryptophan | 0.255 | 0.329 | 0.800 | 0.407 | 0.420 | 0.166 | 0.359 |
| total | 100.000 | 100.000 | 100.000 | 100.000 | 100.000 | 100.000 | 100.000 |

The conditions of the enzymatic hydrolysis (protease used), of the basic treatment (NaOH or KOH) as well as the insects used influence the amino acid composition of the resulting chitin.

EXAMPLE 5: OBTAINING CHITOSAN ACCORDING TO THE INVENTION FROM DIFFERENT INSECTS

•Grinding of the Chitin

Each chitin obtained in Example 4 is finely ground in a centrifugal grinder (Retsch® ZM200) with a strainer with pores of 250 µm.

•Deacetylation of the Chitin

A mass of $m_4$ g of the chitin obtained after the grinding step and a volume $V_2$ ($V_2 = m_4 * 50$ mL) of aqueous sodium hydroxide (or potassium hydroxide) solution with a concentration equal to 19.0 mol·$L^{-1}$ are placed in a 2-L three-neck flask equipped with a condenser and a stirrer (Heidolph® RZR1). The medium is heated with an oil bath to a temperature of 100±2° C. for 2 hours. Throughout the reaction, the reaction medium is subjected to a stirring of 300 rpm.

•Recovery of the Chitosan

The reaction medium obtained at the end of the deacetylation step is then filtered (SEFAR MEDIFABR 03-60/42 filter) so as to recover the chitosan.

•Washing of the Chitosan

The chitosan recovered is then rinsed with tepid tap water until neutralization of the pH.

It is then made to react again in a three-neck flask containing the same quantity of aqueous sodium hydroxide (or potassium hydroxide) solution and the 3 preceding steps (deacetylation, recovery and washing) are repeated identically.

•Drying of the Chitosan

The steps of deacetylation, recovery and washing are therefore carried out twice in total. At the end of these steps, the chitosan is dried for 24 hours, at 60° C., in a drying oven (Binder®, FP53 model). A mass $m_5$ of chitosan is collected. The yield is calculated as follows: $m_5/m_4 * 100$ and the results are summarized in Table 12. In particular, Table 12 refers to a ratio of base:chitin:water, which is a ratio by dry weight in g for the base and the chitin, and by weight in g for the water.

TABLE 12

Masses of chitin, volume of base and yield for obtaining chitosan depending on the insects

| Source of chitin | Base | Initial mass $m_4$ of chitin (g) | Volume $V_2$ of base used (mL) | Ratio of base:chitin:water | Mass $m_5$ of chitosan obtained (g) | Yield (%) |
|---|---|---|---|---|---|---|
| T. molitor (Prolyve + NaOH) | NaOH | 9.98 ± 0.04 | 499 ± 2 | 38:1:50 | 5.59 ± 1.24 | 56.0 ± 12.6 |
| T. molitor (Food Pro + NaOH) | NaOH | 15.04 ± 0.01 | 752 ± 1 | 38:1:50 | 10.35 ± 0.06 | 68.8 ± 0.5 |

TABLE 12-continued

Masses of chitin, volume of base and yield for obtaining chitosan depending on the insects

| Source of chitin | Base | Initial mass $m_4$ of chitin (g) | Volume $V_2$ of base used (mL) | Ratio of base:chitin:water | Mass $m_5$ of chitosan obtained (g) | Yield (%) |
|---|---|---|---|---|---|---|
| T. molitor (Alcalase + NaOH) | NaOH | 18.02 ± 0.02 | 901 ± 1 | 38:1:50 | 12.58 ± 0.07 | 69.8 ± 0.5 |
| T. molitor (Prolyve + KOH) | KOH | 18.58 ± 0.18 | 929 ± 9 | 53:1:50 | 12.70 ± 0.02 | 68.4 ± 0.8 |
| P. marginata (Prolyve + NaOH) | NaOH | 27.71 ± 3.32 | 1385 ± 166 | 38:1:50 | 19.26 ± 2.55 | 69.5 ± 0.9 |
| Z. morio (Prolyve + NaOH) | NaOH | 23.51 ± 0.04 | 1176 ± 2 | 38:1:50 | 16.60 ± 0.53 | 70.6 ± 2.4 |
| G. mellonella (Prolyve + NaOH) | NaOH | 18.58 ± 1.39 | 929 ± 70 | 38:1:50 | 12.85 ± 1.00 | 69.2 ± 0.2 |

The chitosans are then analyzed according to the analysis methods indicated in point II of Example 1. The analysis results are given in Table 13, in which the ash, lipid and amino acid contents correspond to contents in grams per 100 g dry matter. In this table, the lipid content measured is at the detection limit.

TABLE 13

Properties of the chitosans obtained from different insects

| Source of chitosan | Molar mass (kDa) | Ash | Lipids | Amino acids | Purity by difference (%) |
|---|---|---|---|---|---|
| T. molitor (Prolyve + NaOH) | 302 ± 15 | 0.97 ± 0.04 | 0.485 ± 0.01 | 0.24 ± 0.06 | 98.305 ± 0.07 |
| T. molitor (Food Pro + NaOH) | 453 ± 14 | 0.35 ± 0.02 | 0.205 ± 0.04 | 0.37 ± 0.03 | 99.08 ± 0.05 |
| T. molitor (Alcalase + NaOH) | 566 ± 23 | 0.525 ± 0.08 | 0.165 ± 0.01 | 0.32 ± 0.10 | 98.99 ± 0.13 |
| T. molitor (Prolyve + KOH) | 496 ± 7 | 1.48 ± 0.18 | 0.255 ± 0.15 | 0.285 ± 0.05 | 97.98 ± 0.24 |
| P. marginata (Prolyve + NaOH) | 395 ± 19 | 1.485 ± 0.50 | 0.48 ± 0.24 | 0.285 ± 0.09 | 97.75 ± 0.56 |
| Z. morio (Prolyve + NaOH) | 359 ± 19 | 0.725 ± 0.06 | 0.495 ± 0.02 | 0.28 ± 0.07 | 98.50 ± 0.10 |
| G. mellonella (Prolyve + NaOH) | 349 ± 10 | 0.705 ± 0.02 | 0.67 ± 0.00 | 0.30 ± 0.04 | 98.325 ± 0.05 |

As the method according to the invention makes it possible to obtain a chitin with a high purity, the resulting chitosan also has this feature, even under different deacetylation conditions.

The invention claimed is:

1. A chitin having purity of greater than 97.75%, wherein the purity is obtained by subtraction of amino acid, lipid, and ash impurity contents from an absolute purity value, wherein the absolute purity value is equal to 100%, and wherein the chitin is from Coleopterans and/or Lepidopterans insects.

2. The chitin of claim 1, containing less than 1.2% by weight amino acids relative to the total dry weight of chitin.

3. The chitin of claim 1, containing less than 2% by weight ash relative to the total dry weight of chitin.

4. The chitin of claim 1, wherein the purity is greater than or equal to 98%, the molar mass is greater than or equal to 800 kg·mol$^{-1}$, and the molar mass is determined using the falling ball viscosity measurement.

5. A chitosan having purity of greater than 97.75%, wherein the purity is obtained by subtraction of the amino acid, lipid, and ash impurity contents from an absolute purity value, and wherein the absolute purity value is equal to 100%.

6. The chitosan of claim 5, wherein the purity is greater than or equal to 97.9%, the molar mass is greater than or equal to 480 kg·mol$^{-1}$, and the molar mass is determined using the falling ball viscosity measurement.

7. A chitin recovered from cuticles separated from soft parts of killed insects that were enzymatically hydrolyzed with a protease that formed a solid residue and that is treated with a strong base comprising:
chitin greater than 97.75% in purity,
wherein the insects are Coleopterans and/or Lepidopterans, and
wherein the protease is selected from the group consisting of aminopeptidases, metallocarboxypeptidases, serine endopeptidases, cysteine endopeptidases, aspartic endopeptidases, and metalloendopeptidases.

* * * * *